(12) United States Patent
Van Hal et al.

(10) Patent No.: US 9,937,004 B2
(45) Date of Patent: *Apr. 10, 2018

(54) HAIR SHORTENING DEVICE

(71) Applicant: KONINKLIJKE PHILIPS N.V., Eindhoven (NL)

(72) Inventors: Robbert Adrianus Maria Van Hal, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 5 days.

This patent is subject to a terminal disclaimer.

(21) Appl. No.: 15/267,500

(22) Filed: Sep. 16, 2016

(65) Prior Publication Data

US 2017/0000561 A1    Jan. 5, 2017

Related U.S. Application Data

(63) Continuation of application No. 12/089,201, filed as application No. PCT/IB2006/053511 on Sep. 27, 2006, now Pat. No. 9,622,817.

(30) Foreign Application Priority Data

Oct. 3, 2005 (EP) ..................................... 05109139

(51) Int. Cl.
*A61B 18/20* (2006.01)
*A61B 18/00* (2006.01)

(52) U.S. Cl.
CPC .. *A61B 18/203* (2013.01); *A61B 2018/00452* (2013.01); *A61B 2018/00476* (2013.01)

(58) Field of Classification Search
CPC ...... A61B 18/20–18/28; A61N 5/06–2005/073

USPC ........ 606/2, 9–13, 17–19; 607/88–94; 30/32
See application file for complete search history.

(56) References Cited

U.S. PATENT DOCUMENTS

| 6,383,177 B1 | 5/2002 | Balle-Petersen |
| 2004/0230258 A1 | 11/2004 | Altshuler |
| 2005/0049582 A1 | 3/2005 | Debenedictis |
| 2007/0093798 A1 | 4/2007 | Debenedictis |
| 2008/0172047 A1 | 7/2008 | Altshuler |

FOREIGN PATENT DOCUMENTS

| WO | 9907438 A1 | 2/1999 |
| WO | 0062700 A1 | 10/2000 |
| WO | 2005011510 A1 | 2/2005 |

*Primary Examiner* — William Thomson
*Assistant Examiner* — Jonathan Kuo

(57) ABSTRACT

A method, system and device for shortening hair with the method including generating a plurality of laser pulses overlapping in time; focusing the laser pulses into spatially separated focal spots having a peak power density at least equal to a first threshold at which a laser induced optical breakdown phenomenon occurs in the hair and below a second threshold at which a laser induced optical breakdown phenomenon occurs in skin. Generating the plurality of laser pulses includes an act of generating the plurality of laser pulses to reach the first characteristic threshold value after a start of each corresponding laser pulse in a time span of less than half of the pulse duration; and positioning the respective at least three focal spots into respective target positions within a single hair such that only one of the plurality of laser pulses occur in each of the at least three focal spots.

15 Claims, 3 Drawing Sheets

HAIR SHORTENING DEVICE

Figure 1:
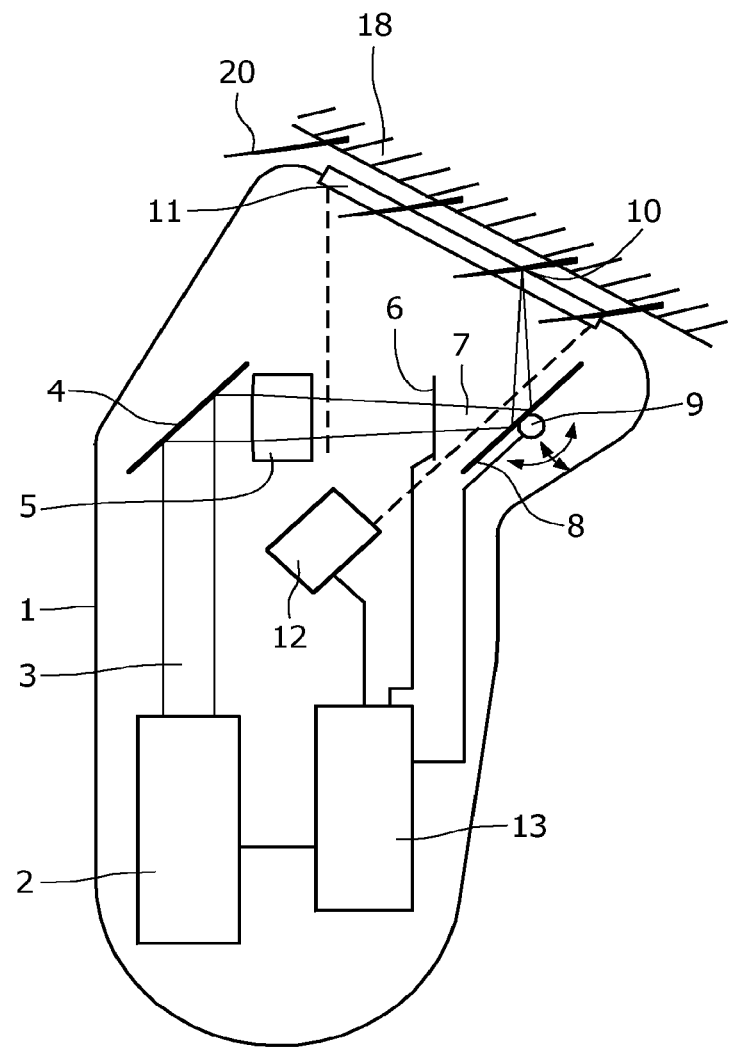

This application claims the benefit or priority of and describes the relationships between the following applications: wherein this application is continuation of prior U.S. patent application Ser. No. 12/089,201, filed Apr. 3, 2008, which is the National Stage of International Application No. PCT/IB2006/053511, filed Sep. 27, 2006, which claims the priority of European Application No. 05109139.5, filed Oct. 3, 2005, each of which is incorporated herein by reference thereto.

The invention relates to a device for shortening hairs. In particular, it relates to a device for shortening hairs, comprising a laser radiation system and an optical manipulator, wherein the laser radiation system is constructed and arranged for providing a plurality of laser pulses focused in respective focal spots, and comprises:

a laser source that is constructed and arranged for generating laser radiation in the form of laser pulses with a predetermined pulse time; and an optical system that is constructed and arranged for focusing the laser pulses into respective focal spots, wherein the optical manipulator is constructed and arranged for positioning the respective focal spots into respective target positions, wherein a power of the generated laser radiation and a dimension of the focal spot are such that, in the respective focal spots, the laser radiation has a power density which is above a characteristic threshold value for hair tissue above which, for the predetermined pulse time, a laser induced optical breakdown phenomenon occurs in the hair tissue.

Document WO 2005/011510 discloses a device for shortening hairs, in which a laser source generates a plurality of laser pulses in a number of adjacent target positions in a such that the pulses each generate a LIOB phenomenon, that in co-operation cause breakage of the hair along said line.

A disadvantage of said device is that the total energy to break the hair is relatively large. This not only means a reduced energy efficiency, but also causes the laser source and its energy source to be accordingly large and complex.

It is an object of the invention to provide a device for shortening hairs with improved energy efficiency.

This object is achieved with a device of the kind mentioned in the preamble, that is characterized in that the radiation system is constructed and arranged for providing at least two of the laser pulses in spatially separated respective focal spots substantially simultaneously.

The inventors have found that by providing at least two of the laser pulses in spatially separated respective focal spots substantially simultaneously, the possibility is provided that the LIOB phenomena in those focal spats may co-operate. This in turn was found to reduce the required energy to break and thus shorten the hair. The providing of, and making use of, this co-operation of mechanical effects is an important aspect of the present invention. Of course, this co-operation will have a larger effect when the focal spots are closer together, or the energy in the focal spots is higher, etc. All this, together with some background on the phenomena, will be discussed below.

The expression "substantially simultaneously" is intended to mean that the mechanical effects of the LIOB phenomenon in one focal spot overlap in time with the mechanical effects of the LIOB phenomenon in another focal spot. In practice, considering the time scales and the possible repetition frequencies of the laser source, this will most often come down to the respective pulses overlapping in time. Preferably, the laser pulses are provided simultaneously.

In general, laser induced optical breakdown (LIOB) occurs in media, which are transparent or semi-transparent for the wavelength of a pulsed laser beam, when the power density of the laser beam in the focal spat exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects such as cavitation and the generation of shock waves, which damage the medium in positions surrounding the position of the LIOB phenomenon.

For a more elaborate description of LIOB, reference is made to document WO2005/011510, in particular pages 2 and 3. From that document, it can be learned that preferred wavelengths for the laser radiation are between approx. 500 nm and 2000 nm, preferably between 800 nm and 1300 nm, even more preferably between 1000 nm en 1100 nm. A useful wavelength is for example the 1064 nm wavelength of an NdYAG laser. Furthermore, the threshold value of the required power density seems to be dependent of the pulse time. This dependency may be determined by the skilled person, and it has been found that a pulse time in the order of for example 10 ns suffices. For this value of the pulse time, the threshold value Dh of the power density in the focal spot in hair is in the order of $4.10^{11}$ W/cm$^2$. It is to be noted that this value is also dependent on the shape of the hair (circular cross section, elliptical cross section etc.) and on some other factors, such as (linear) absorption. It is furthermore to be noted that in the literature, the claimed values for LIOB threshold values differ widely, even over three orders of magnitude. To be precise, these values relate to the LIOB threshold value in water. For the present invention, it is assumed, as seems to be supported by evidence found by the inventors, that the LIOB threshold value in water substantially corresponds to that in skin tissue, which is a rather watery tissue. Although the difference in LIOB threshold values found may be connected to issues such as pulse quality and profile, measuring techniques etc., it suffices to say that a skilled person will find an appropriate setting of the laser and the optical system to obtain LIOB.

A further remark about the present device is that a number of parts is not elaborated further. This holds in particular for an image (hair) recognition system, with an optical window in the housing of the device, a control unit for controlling the laser source and the optical manipulator, based on images of the image recognition system etc. A detailed description of the image recognition system and its operation and the control system is omitted here for the sake of simplicity. However, reference is made to WO-A-00/62700. The hair-removing device described therein has a similar image recognition system and control system, and the operation thereof is described in detail therein. On the basis of said description in WO-A-00/62700, the person skilled in the art will be able to design and adapt any image recognition system and control system so as to he suitable for their purpose in the present device.

In addition to the energy reduction, the present invention also provides an advantage in that reduction of the energy in the individual focal spots is safer for the skin, which results in more freedom to design the device. Furthermore, the prior art device with consecutive pulses results in relatively rough cutting edges of the remaining stubble, which is undesirable, as this can be the basic cause for the occurrence of ingrown hairs.

There are various ways to provide at least two focal spots of laser radiation substantially simultaneously. In a first embodiment, the laser source is constructed and arranged for providing a plurality of laser beams substantially simultaneously. In this case, a plurality of laser subsources may be present, for example each being controlled substantially simultaneously to emit laser radiation. This offers optimum freedom of design, and has a further advantage that it is very simple to ensure that the emitted laser beams are emitted parallel.

In another particular embodiment, the optical system comprises a beam multiplier element that is constructed and arranged for multiplying an incident beam of laser radiation into a plurality of simultaneously outgoing laser beams. When taking a single beam of laser radiation, or a small number of such laser beams, and multiplying them into a plurality of outgoing laser beams, it is very easy to ensure simultaneous emission thereof. Furthermore, since only a single laser source or a small number of laser sources is required, the design of the device may be relatively simple and compact.

In a particular embodiment, the optical system comprises a grating. As is well known in the art, a grating is able to split up an incident beam into a plurality of beams, according to the different orders of the grating. Alternative systems to the grating are for example beam splitters, semitransparent mirrors and so on. All these optical systems may provide a plurality of simultaneously outgoing laser beams with substantially the same power or with different powers, depending on their design For example in the case of the grating, which is preferably a phase grating in view of the power densities that the grating has to handle, it is possible to provide substantially equal powers for the outgoing laser beams by appropriate design of the transmission or reflection profile of the grating, and in particular the thickness profile of the phase grating. This is well known in the art.

In a special embodiment, the beam multiplier element is moveable, preferably rotatable or pivotable. In particular, the beam multiplier element is moveable such that it allows the focal spots of the simultaneously outgoing laser beams to be correctly positioned with respect to a hair to be shortened. It was found by the inventors that it is advantageous to provide the focal spots in a plane or on a line, that extends substantially perpendicularly to the direction of the shaft of the hair. This is not only due to the fact that, in that case, the cross sectional surface area or diameter of the hair is smallest. It also relates to a phenomenon observed by the inventors that relates to preferred direction of fracture. As will be explained in the description of the figures, in particular FIG. 5a-c, preferred directions of fracture of a hair are along the direction of the club or shaft of the hair, and in a plane perpendicular thereto. Hence, if the line connecting the adjacent focal spots coincides with a preferred direction of a fracture, the greatest effect of co-operation between the mechanical effects of LIOB in the adjacent focal spot is obtained. In that case, the least energy is required to shorten the hair. Providing a moveable beam multiplier element is one way to provide the focal spats in such a position. Rotating serves to adapt the position of the focal spots in one direction, while pivoting adapts the position in two directions. It is noted that pivoting can he used for e.g. semitransparent mirrors, but not without limitations for gratings, since the latter are designed for a certain angle of incidence, most often perpendicular incidence. However, rotation around the direction of the incident beam is possible.

An alternative could be an appropriate design of the optical manipulator. Since the optical manipulator was designed from the onset for positioning the respective focal spots into respective target positions, it is relatively easy to incorporate the desired functionality into its mechanisms. For a basic discussion of such an optical manipulator, reference is made to WO-A-00/62700.

In a special embodiment, the number of simultaneous focal spots is between 2 and 20. Although in principle the number of focal spots is not limited, a number between 2 and 20 was found to be such that a beneficial effect of co-operating mechanical effects of LIOB in focal spots is obtained, while preventing a complex design of the device. In practice, the number of focal spots will normally equal the number of target positions and also equal the number of laser pulses, which in this case are all provided substantially simultaneously. Note that this need not be the case, since two or more substantially simultaneous laser pulses of a larger total number of laser pulses may already give a beneficial effect. For example, it is already advantageous to provide two or more bursts of laser pulses, as long as in at least one of those bursts there are at least two substantially simultaneous laser pulses.

In a particular embodiment, the grating is able to provide between 2 and 20 outgoing laser beams for each incident laser beam. In principle, any desired number of outgoing laser beams may be provided by a single grating or combined grating. However, numbers between 2 and 20 outgoing laser beams seem appropriate in order to limit the complexity of the grating. Note that it is possible to provide even numbers of outgoing laser beams e.g. by covering a desired number of outgoing laser beams, such as the central beam of zero-th order.

In a particular embodiment, a distance between adjacent simultaneous focal spots is at most equal to an effective mechanical working distance of the laser induced optical breakdown phenomenon in the focal spats. This relates to an elaboration of the co-operation of the mechanical effects of the LIOB phenomenon caused in the focal spots. The mechanical effects are believed to be shock waves and/or cavitation in the hair tissue. These may cause damage to the hair, which will eventually break the hair. Such shock waves and cavitation will produce damage to the hair over a certain distance, which is dependent on power density and pulse time, and also on the direction in the hair (preferential direction of fracture). Although it is hard to predict exact values for the effective mechanical working distance, since the mechanism is not completely understood, it is relatively easy to determine this effective mechanical working distance in practice. Simple experiments will teach the skilled person an appropriate value of the effective mechanical working distance for selected settings of the laser, such as peak power density, pulse power profile and pulse time, and the number of focal spots. Another factor that may influence the effective mechanical working distance is, as mentioned above, the direction in the hair. The effective mechanical working distance will be larger along a preferential direction of a fracture in the hair. Below, as well as in the description of the figures, some experimental values are given.

In particular, said distance between adjacent focal spots is selected to be at most equal to the diameter of a hair to be shortened, divided by the number of simultaneous focal spots. By thus providing the simultaneous focal spots in a regular distribution, preferably along a straight line, even more preferably perpendicularly to the direction of the club or shaft of the hair, a high efficiency of LIOB shortening of the hair is ensured. This technical feature will imply a certain design for the optical system, which is easily determined by the skilled person. Note that in the above case, all focal spots are present in the hair. This is not strictly necessary, as will be explained in some cases herein below. However, if all focal spots are present in the hair, in principle all of the energy absorbed therein may be used for shortening the hair, which increases the efficiency. In another preferred embodiment, the focal spots have a maximum distance between each other that equals the diameter of an average hair, in particular about 100 µm. Note that this includes the case that adjacent focal spots are much closer than the maximum distance. It is of course possible to select a different value of the maximum distance, corresponding to a different value for the maximum hair diameter, for example 150 µm. This latter value covers most types of hair across the body and even across the human race.

In a particular embodiment, an energy in each laser pulse is such that said mechanical working distance is between 5 and 50 µm, preferably between 10 and 25 µm. In this case, the values for the effective mechanical working distance are based on a preferred number of focal spots, viz. between 2 and 20, and an average diameter of a human hair, viz. 100 µm. Of course, if a different value for the diameter of the hair is taken, such as 150 µm, or a different number of focal spots is assumed, the effective mechanical working distance should be adapted accordingly.

It is noted that in the description of the invention and in the claims, the required dimension of the focal spot, the required power of the generated laser radiation and, above, the energy and the effective mechanical working distance are defined in terms of the result to be achieved, such that, in the focal spot, a LIOB phenomenon occurs in hair tissue or such that the mechanical effects of said LIOB phenomenon overlap for adjacent focal spots. It is however noted that, for a given laser source with a predetermined pulse time and pulse energy, and for a given number of focal spots and a given hair dimension, a skilled person will be able to determine the required dimension of the focal spot on the basis of the pulse time, the pulse energy, if necessary the pulse power profile and the characteristic threshold value for LIOB, or the geometry of the hair and the number of the focal spots in the hair, respectively. With that information, the skilled person will be able to design a suitable optical system which provides the necessary dimensions of the focal spot or the required geometry or pattern of the focal spots in the hair. It will further be obvious for the skilled person that, if a laser source is used having a shorter pulse time or a more efficient pulse power profile, or an optical system providing a higher number of focal spots, corresponding amendments to the focal spot (pattern) may be made. As stated before, simple experiments will show the skilled person the way to those amendments.

In order to provide some figures, and some rules of thumb, a number of particular values is given below. In particular, the present device is constructed and arranged to provide a total energy E that is absorbed in all focal spots of the laser pulses in a hair Which is lower than a corresponding total energy E(pa) that is absorbed in the case wherein all the laser pulses would have been supplied consecutively, In a special embodiment, said total energy E is at least 10% less than 4 mJ for an average human beard hair, and preferably is about 2 mJ for an average human beard hair. These embodiments express that the present invention allows a more energy efficient shortening of the hairs due to the co-operation of the individual focal spots. Since the energy to shorten or break a hair depends on various factors, notably the diameter of the hair and also the pulse power profile, linear absorption properties of the hair etc., it is best to determine the appropriate values for the various types of hair experimentally. For an average human beard hair, having a diameter of about 100 µm, the typical energy to break the hair with the prior art device is about 4 mJ.The present device allows a substantial energy reduction, which amounts to at least 10% and may be as large as 50% or even larger. This accounts for the value of about 2 mJ, in practice between 1.5 and 3 mJ, for the average human beard hair.

In a particular embodiment, the simultaneous focal spots are provided in a 3D pattern, preferably a tetrahedron, extending in or through the hair to be shortened. By providing a 3D pattern, which may be regular or irregular, the sensitivity of the device as to the orientation of the hair is reduced. For example, when the focal spots would be provided in a plane that makes a very small angle with the direction of the shaft of the hair, it may turn out to be rather difficult to break the hair. However, when a 3D pattern of focal spots is provided, it is easy to always provide a plane of focal spots that makes a large angle with said direction, preferably at least 60-90° therewith. This ensures that there is always an efficient area of focal spots to break the hair. The tetrahedron, or a regularly arranged area of tetrahedrons, is such an efficient 3D area of focal spots.

In another particular embodiment, the simultaneous focal spots are provided in a plane that extends through a hair to be shortened, preferably substantially perpendicularly to the direction of the shaft of the hair. If the focal spots are provided in a plane, their number can be limited, when compared to the 3D pattern. It is then preferred to provide said plane to extend substantially perpendicularly to the direction of the shaft of the hair. In this context, "substantially perpendicularly" means "at an angle of at least 60°, preferably 90°", with respect to said direction. Other directions are not excluded, but may require more focal spots, and are hence less energy efficient. Note furthermore that the plane need not be perfectly smooth or plane, although such a non-smooth plane could also be considered a 3D pattern.

In a particular embodiment, the simultaneous focal spots are provided in a triangular pattern, preferably an equilateral pattern. Similar to the discussion above of the tetrahedron, a triangular pattern, and preferably an equilateral triangular pattern offers an efficient pattern in 2D to ensure a low sensitivity as to the orientation of the hair.

In a special embodiment the simultaneous focal spots are provided on a line extending through a hair to be shortened, preferably substantially perpendicularly to the direction of the shaft of the hair. Herein, the line need not be straight, although a non-straight line could also be considered a 2D or 3D pattern. Furthermore, the expression "substantially perpendicularly" has the same meaning as in the case of the plane mentioned above. Preferably, the line extends through the center of the hair to be shortened. This ensures that the least amount of energy is required to cut the whole hair. "Through the center of the hair" comprises the case in which the line has a distance of no more than 15 µm, preferably no more than 5 µm, to the center of the hair. Note, however, that the center or medulla of the hair is in itself mainly a soft, fatty tissue with mechanical properties which are less suitable for the generation and transport of the mechanical effects that accompany LIOB, for shortening the hair. Hence, providing focal spots inside the medulla is less efficient, and is preferably prevented. For that reason, the pattern of focal spots in the hair may be adapted. accordingly, such as only outside the medulla. Note, however, that not every hair has a medulla. It is also possible to supply more energy to any focal spot in the medulla, to compensate for the lower efficiency of LIOB inside the medulla. Such increased energy for a central focal spot may for example be provided by a suitable design of a grating or other optical element.

In a particular embodiment a peak power density in a focal spot during a laser pulse is selected to be at least equal to a characteristic threshold value Dh for hair tissue above which, for the predetermined pulse time, a laser induced optical breakdown phenomenon occurs in the hair tissue, but below a characteristic threshold value Ds for skin tissue above which, for the predetermined pulse time, a laser induced optical breakdown phenomenon occurs in the skin tissue. By selecting the peak power density above the threshold value Dh, an LIOB phenomenon can be generated in the hair. However, since the peak power density is also selected to be lower than the value Ds for a skin tissue, no LIOB phenomenon will be generated in the skin. Hence, no negative mechanical effects will be caused in the skin. This will prevent pain and other discomfort, and is inherently more safe. Herein, use is made of the fact that the threshold value Ds is higher than the threshold value Dh.

In particular said peak power density is between 60% and 95% of Ds, preferably between 70 and 85% of Ds. It was found by the inventors that 60% of Ds is a useful lowest peak power density, although in sonic cases even lower values might be used. Furthermore, 95% of Ds proved a sufficiently safe value of the highest peak power density. Preferably, in order to be on the safe side for substantially all skin and hair types, the peak power density is selected to be between 70 and 85% of Ds. In this range, LIOB is reliably generated in most types of hair, while LIOB is reliably prevented in most types of skin tissue.

In a particular embodiment, said peak power density is between $4 \cdot 10^{11}$ W/cm$^2$ and $7.5 \cdot 10^{11}$ W/cm$^2$, preferably between $5.5 \cdot 10^{11}$ W/cm$^2$ and $7 \cdot 10^{11}$ W/cm$^2$. Note that the above values are also dependent on pulse time. In general, a shorter pulse time requires a higher peak power density. The values given hold for pulse times between about 1 and 20 ns, in particular for values of 8-10 ns. The skilled person will have no trouble in adapting the peak power density values to those that correspond to different pulse time.

These values have been determined by the inventors to correspond to the above-mentioned ranges of 60% to 95% of Ds, and 70-85% of Ds respectively, Herein, the value Ds as determined by the inventors is about $8 \cdot 10^{11}$ W/cm.$^2$. As mentioned above, there is a large discrepancy between the value for the LIOB threshold value in water, as determined by various research groups, and which value for the present invention is assumed to correspond substantially to the value of Ds. It is however noted that the indicated ranges for the ratio between the peak power density and the value for Ds in principle hold independent of the actually measured value of Ds. This makes use of the fact that whatever factor influences the measurement of Ds, this will also, and in a similar fashion, influence the measurement of Dh.

In a special embodiment, a temporal profile of the power density of the pulse is such that the peak power density, and preferably the threshold value Dh, is reached after a time after the start of the pulse that is less than half the duration of the pulse, preferably after a time that is less than 25% of the pulse duration. This step of providing the power density with a certain temporal profile is sometimes called "pulse shaping" or "pulse engineering". The principal itself is well known to the skilled person in the field of laser technique, or electrical engineering in general. An example of a technique that may be used in pulse shaping is slow Q-switching of the laser source. Other examples will be readily found by the skilled person.

The effect of pulse shaping will be that a larger part of the energy is coupled into the plasma. This is due to the fact that, in LIOB, optical energy is (substantially) only absorbed by a plasma, which in turn is generated by the presence of a sufficiently high power density of optical energy, viz. the threshold value. If the pulse would be symmetrical, and the peak power density would equal the threshold value, then about half of the energy of the pulse would be absorbed in the plasma. In other words, the remaining half of the energy would be transmitted by the tissue without absorption, apart from linear absorption. By shaping the pulse such that the power density reaches the threshold value earlier, i.e. before half of the pulse duration, a larger part of the pulse energy may be absorbed by the plasma. This may of course be caused by selecting a peak power density, which is (much) larger than the threshold value. However, it is disadvantageous, although not excluded, so increase the peak power density above the threshold value Ds for skin tissue, for the reasons already mentioned above. By appropriate pulse shaping, it is possible to quickly increase the power density up to or above the value Dh, but subsequently keeping the pulse at a relatively high level for a relatively long time, almost no energy is lost during the time before the plasma of the LIOB is generated. In principle, a power density ramp that is as steep as possible would be preferable. However, the pulse shape in which the threshold value Dh is reached before half of the duration of the pulse, preferably at the latest at 25% of the pulse duration, is already advantageous.

In another particular embodiment, a temporal profile of the power density is such that more than 50%, preferably more than 70%, of the energy in the pulse is delivered to the focal spot after reaching the peak power density. This embodiment takes account of the fact that the energy in the pulse may only be absorbed by the plasma. In other words, only during presence of the plasma it is possible for optical energy to be absorbed. However, the plasma has a very short life due to recombination of the generated ionized particles. Without energy added during the lifetime of the plasma, an average half-life (recombination time) of the plasma is a few ns. Hence, it is less advantageous if, in the pulse, the power density would reach the threshold value Dh in a very short time, after which the power density drops to a value that is much lower than this threshold value, since in that case a large part of the plasma would recombine, and thus disappear, rather quickly. This would deprive the plasma of the possibility to absorb the energy in the rest of the pulse. Hence, it is advantageous to maintain the power density in the pulse after reaching the threshold value Dh at a relatively high level, for example at least 75% of Dh. All this depends on the specific properties of the plasma, which in turn are dependent of the (peak) power density etc. However, useful power density profiles for the pulse may readily be determined by experiment.

These and other aspects of the invention are apparent from and will be elucidated with reference to the embodiments described hereinafter.

Figure 2:
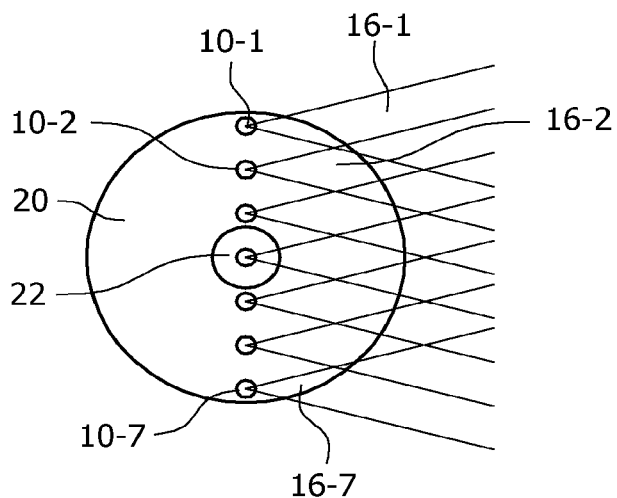
Figure 3A:
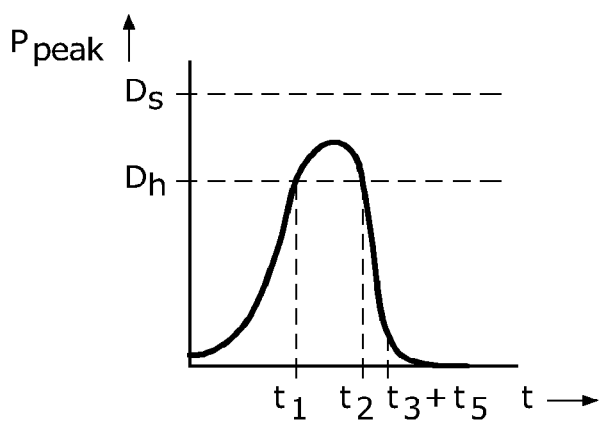
Figure 3B:
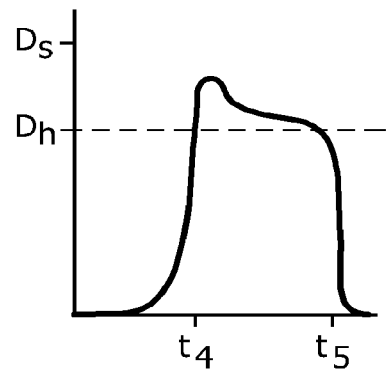
Figure 4:
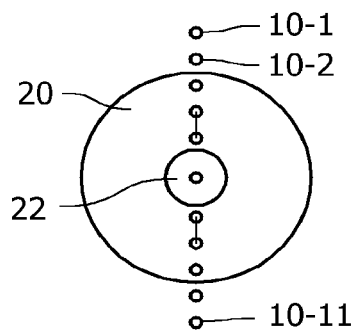
Figure 5A:
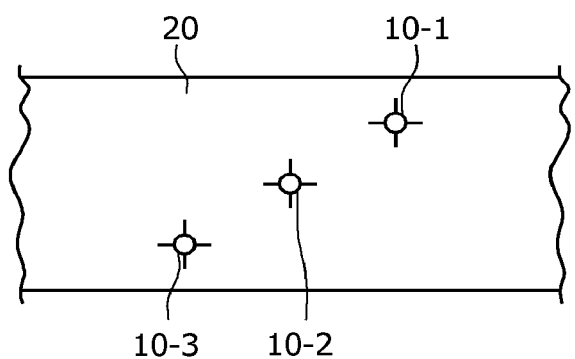

In the drawings:

FIG. 1 diagrammatically shows an embodiment of a device according to the invention;

FIG. 2 diagrammatically shows a cross-sectional view of a hair being shortened by a device according to the invention;

FIGS. 3a, b shows the temporal profile of the peak pulse power for a normal Gaussian pulse (3a) and for an engineered pulse (3b);

FIG. 4 diagrammatically shows across-sectional view of a hair being shortened by another embodiment of a device according to the invention; and FIGS. 5a, b and c show typical damage patterns of a hair at three different amounts of totally supplied energy.

FIG. 1 diagrammatically shows an embodiment of the device according to the invention.

The device comprises a housing 1 with a laser source 2, emitting a laser beam 3 that is reflected (optionally) by an optional fixed mirror 4 and passes an optical focusing element 5 and beam multiplier element 6, to become a plurality of focused laser beams 7 (only one is shown). The plurality of focused beams 7 is reflected mirror 8 that is moveable around pivot 9. Each of the plurality of focused laser beams forms a focus 10, and leaves the housing 1 through optical window 11.

A CCD-camera is denoted by 12, and is connected to a control unit 13, that is also connected to the laser source 2 and the mirror 8.

Furthermore, reference numeral 18 denotes skin, with a number of hairs 20.

The housing 1 may be any type of housing that fits the parts. It may be made of any desirable material or combination thereof, such as metal or plastic. In particular for consumer use, it may have the shape of a common electrical shaver, although other shapes are not excluded.

The laser source 2 may in principle be any desired laser source that emits in a desirable wavelength region of roughly between 500 nm and 1500 mn. In particular, it comprises a NdYAG laser emitting at 1064 nm, or other suitable solid state laser, or other type of laser. Preferably, but not exclusively, the laser is a pulsed laser, that is able to emit pulses with a period of about 0.1 ns-100 μs. The power density is preferably such that in such a period, the emitted laser beams are able to start a LIOB in a hair. Since the peak power density strongly depends on the focusing optics, it is not possible to base a strict power criterion on this condition. However, in order to cut a hair, the focused laser beam(s) should preferably be able to provide a few mJ in that same period to an average hair. The total energy to cut through a hair depends on the diameter of the hair, but it is safe to assume a lower power limit of 1 mJ in the focused laser beams during 100 μs. Note that the power density need not be a constant during that time period. As discussed above, pulse shaping is advantageous.

The power source for the laser source 2 has not been shown. It may be any type of power source, such as a battery, or an external connection, such as to mains, et cetera. It is also possible to provide the laser source 2 as an external source, such as a separate laser unit, e.g. for heavy duty applications, in beauty parlors et cetera. In such a case, the emitted laser beam may be coupled into the device by means of a fiber coupling, mirrors and so on.

In the present device, the laser source 2 emits a laser beam 3 that is reflected by fixed mirror 4. In principle, this mirror 4 is optional, and serves here only to aim the laser beam 3 at the moveable mirror 8. In other cases, with a different set-up for the laser source, it may be omitted.

The optical focusing element 5 is e.g. a lens, preferably with a high damage threshold and optimized for the laser wavelength as to focusing properties and transmission. This latter condition holds for all optical parts of the device, in view of the rather high power density. Note that it is also possible to combine the optional mirror 4 and the optical element 5 into one optical element, such as a focusing mirror.

The beam multiplier element 6 is in this case a phase grating, i.e. a grating made of a transmissive material and having a thickness that varies across its width. Due to the phase differences caused by the extra path length through the material, the interference effects ensure that the incident single laser beam is turned into a number of subbeams. By appropriate shaping of the phase grating, it is possible to provide each of the subbeams with a substantially equal power (density), although this is not strictly necessary. The number of subbeams also depends on the exact shape of the phase grating. Alternatively, it is also possible to use semi-transparent mirrors, optical beam splitters etc., to obtain a number of subbeams.

In the case of a phase grating, and the other beam multipliers, it may be advantageous to redirect the subbeams to run in a desired direction, to be able to aim the subbeams and their foci at the hair to be shortened. Thereto, an additional optical element (not shown), such as a lens or a multiple lens, or one or more mirrors, may be provided after the beam multiplier element 6. A preferred direction is a parallel direction, although this is not strictly necessary. It is also possible to provide a suitable focusing element 5 after the beam multiplier element 6, so that it is possible to combine the subbeam redirection action and the focusing action in one element, or at least one group of parts in the device.

Optionally, the beam multiplier element 6 is moveable, e.g. around abeam multiplier pivot (not shown) and is then connected to the control unit to control the movement. This embodiment is useful in order to be able to shorten hairs that are present at an undesirable angle with respect to the focused subbeams. Moving, such as rotating, the element 6, such as the phase grating, makes it possible to locate the foci 10 that correspond to the focused subbeams at a suitable angle with respect to the hair 20. Note that it is also possible to perform this focus locating action by other means, such as by appropriate positioning of the moveable mirror 8 to be discussed herebelow, or by means of an additional optical element (not shown) just before the optical window 11.

The moveable mirror 8 is moveable around a pivot 9 by means of one or more actuators (not shown). This enables the focused (sub)beams to be aimed at a desired position with respect to the device, or in other words enables to select a hair to be shortened. Note that it is also possible to use two or more separate mirrors instead of a single mirror 8, e.g. if it is desired to simplify control in x- and y-directions.

The mirror 8, or more precisely: the actuators therefore, is connected to a control unit 13 for controlled movement of the mirror. This may be a suitable microcomputer or other circuitry.

In order to enable control, the device also comprises an image recognition system, such as e.g. the "aim-and-shoot"-device disclosed in WO-A-00/62700, in particular the hair recognition system and the system part to direct the (sub) beams towards the desired part of the hair to be shortened. In the present case, said system comprises a CCD camera 12 and e.g. hair recognition software in the control unit 13 for evaluation of the image of the skin 18 with hairs 20. If desired or necessary, the skilled person will be able to adapt such image recognition and control system to his needs. The control system will also be connected to the laser source, for control thereof. Note that an image recognition system may be omitted e.g. if the laser beam(s) scan(s) the whole skin with peak power levels in the foci that cause LIOB in the hair but not in the skin. However, in view of energy efficiency and prevention of possible skin irritation et cetera, the embodiment with a hair recognition system is advantageous.

Alternatives to a CCD camera 12 are a CMOS based camera and so on. The field of view will be similar to the field of exit of the focused beams and their foci 10, and will be apart of the optical window 11, through which said focused beams leave the device. The optical window could simply be an opening in the housing 1 of the present device, or could be made of an optically transparent material. Preferably, the material is able to withstand the high power density, hence has a high transmission at the wavelength used. Advantageously, the optical window 11 is made of a material such as sapphire, which has a useful coefficient of thermal conductivity, and is thus able to efficiently cool the skin. Other materials, such as various types of glass are also possible.

In use, say to shave a male's beard, the device, as a whole will be moved across the skin. The CCD camera 12 will take images from the skin, The control unit 13 will evaluate the images, and determine the position of a hair 20 to be shortened. The control unit will then control the position of the mirror 8 and fire the laser source 2 such that the foci 10 of the focused subbeams will be aimed at said hair 20, in order to let the LIOB related phenomena at those foci 10 break the hair 20. A realistic frequency for the loop comprising recognition of a hair, moving the mirror 8 and possibly other elements such as phase grating 6, and for firing the laser source 2 is about 100 Hz. Of course, this number strongly depends on the velocity with which the device is moved across the skin, the hair density, the speed of the control unit 13 and so on, and should thus not be considered limiting the invention. Nevertheless, with the said Hz loop frequency, it is possible to shave a male's beard, with on average about 12,000 hairs, in about 2 minutes.

FIG. 2 diagrammatically shows a cross-sectional view of a hair being shortened by the device of the invention. The hair 20 has a central part or medulla 22. There are seven foci 10-0 through 10-7 from seven focused laser beams 16-1 through 16-7.

The number of foci 10 is not limited to seven, but may, in principle, be any plural number, such as 2, 3, and so on. The laser beams, and thus the foci 10, are supplied substantially simultaneously. That is, at such times that the mechanical effects of the LIOB phenomenon of at least two of the plurality of foci 10 overlap one another.

The foci 10 are shown located on a substantially straight line. However, it is also possible to locate them on an undulating or otherwise irregular line. In fact, it is also possible to provide the foci 10 in a 2D or 3D pattern, regular or irregular. A straight line, that is well positioned with respect to the hair, has the advantage that the least number of foci is required, as compared to other patterns of foci with each an equal energy density.

A useful 2D pattern could he in the shape of a equilateral triangle (not shown here), because such a pattern is rather insensitive to angular positioning of the beams with respect to the hair 20. In fact, any 2D pattern, with foci 10 in a plane that intersects the hair 20, is less sensitive as to angular orientation as compared to the straight line. Of course, the energy efficiency will be somewhat less in most cases, since either the average distance between foci 10 increases, or their absolute number or energy each, or a combination of these factors. Similar considerations hold for 3D patterns, as discussed above, and of which an isosceles tetraedron is an example (not shown).

FIGS. 3a, b shows the temporal profile of the peak pulse power for a normal Gaussian pulse (3a) and for an engineered pulse (3b).

FIG. 3a shows a normal Gaussian pulse and its power delivered in the focus. The peak power increases smoothly to a threshold value Dh where the LIOB phenomenon in hair starts and continues to increase to its peak value, which should preferably remain below the LIOB threshold value Ds in skin, Note that this need not be the case when it is made certain that all foci are present in hair, or if LIOB in skin is allowed, e.g. if the number of LIOB phenomena in skin is very low). Since the peak pulse power is only slightly higher than Dh, and the pulse is symmetrical in time, only about half of the available energy may be coupled into the plasma, that only exists after the time t1, where the threshold value is first reached. In fact, energy may only be coupled into the plasma while said plasma exists. The plasma is formed at t1, i.e. the time of reaching the LIOB threshold, and exists until t3=t2+tr, i.e. until a plasma recombination time tr after time t2 where the power density drops below said threshold. Although said recombination time is dependent on a number of factors, such as peak plasma particle density and in fact also on the amount and density of energy coupled into the plasma, an average recombination time tr will be about a few (1-10 ns).

FIG. 3h shows a pulse with an "engineered" power density profile. The power density is increased very quickly until time t4, to a value above the LIOB threshold Dh in hair, but still below the LIOB threshold in skin, again this not being strictly necessary. After that, and until a time is t5=t4+tr, energy may be supplied to the plasma. Since now only little energy is lost during the first phase of the pulse, before reaching the threshold Dh, the energy efficiency may be almost doubled. It is noted here that this is rather a theoretical issue, since there are a number of power densities that play a role in the plasma behaviour, such as an initial multiphoton effect threshold value, a threshold at which the plasma is able to develop et cetera. Since these values are furthermore rather difficult to measure, the relevance of these thresholds for the present application is not yet very great.

Techniques for such pulse shaping are known to the skilled person. Reference may be made to slow Q-switching of the laser and so on. It is noted that said pulse engineering may be optimized depending on e.g. the ratio of pulse time t_pulse and plasma recombination time tr, etc. For example, if t_pulse is much longer than tr it is important to supply as much energy as possible in the time immediately after the time of reaching the LIOB threshold Dh. Contrarily, if tr is much longer than t_pulse, this seems hardly relevant. Since practical, though non-limiting values for tr and t_pulse are 2 ns and 10 ns, respectively, pulse engineering may very well prove worthwhile.

FIG. 4 diagrammatically shows another embodiment of the method. Herein, a hair 20 is shown, and there are 11 foci 10-1 through 10-11 present over a length of 200 μm. The number of foci nor the length should be construed as limiting, to be explained below.

The diameter of hair varies over the different parts of the body, and the different types of hair. For example, a beard hair is much thicker than a vellus hair on the forehead. A maximum diameter of a human hair is about 120-150 μm, although incidentally thicker hairs may be found. With the device of the present invention, it is of course possible to build in feedback on the diameter of the hair, and to adapt the position of the foci accordingly. However, this takes a considerable amount of computing power and time. Now, by providing a line of foci 10 over a length of say 120-150 µm, and with peak power densities in the foci 10 between the LIOPB threshold value in hair Dh and in skin Ds, it is possible to use one setting for all hairs. For should a number of foci fall outside a hair, it is true that the energy is lost for the shortening action, but, on the other hand, the power density is not high enough to cause LIOB, and thus damage or pain, in the skin. Furthermore, there is still sufficient energy to shorten the thinner hair, since the amount of supplied energy will decrease about linearly with the number of foci in the hair, while the required energy decreases roughly with the square of the diameter, or at least more quickly than linearly.

Furthermore, by providing the foci over a distance of even more than those 120-150 µm, such as e.g. the 200 µm mentioned above, it is also possible to shorten the thickest hairs without very accurate positioning of the foci. In this way, it is possible to account for inaccuracies in the positioning of the foci, or in the hair recognition system. In use this improves the speed of the device as a whole.

FIGS. 5a, b and c show, in a longitudinal sectional view, typical damage patterns of a hair at three different amounts of totally supplied energy. In each case, three foci are used, and an average hair of 100 µm diameter is used, for which, say, 2 mJ would be required to cut the hair. Furthermore, the foci are located on a line that makes an angle of about 45° with the longitudinal direction of the hair, to be able to show the specific fracture behaviour. This would not, or much less so, be visible when the foci would be located on a line perpendicular to the longitudinal direction of the hair.

FIG. 5a shows the case wherein the energy supplied to the foci was too low, say 0.5 mJ in total. The hair is not broken, although damage is visible in the form of short lines of fracture and a small surface of fracture, both of which are visible as short lines in th s view, to be precise the two horizontal lines, and the two vertical lines, respectively, for each focus. it was found that these are the preferential directions in which damage to the hair, viz. the fractures, occurs, namely the direction parallel t the shaft of the hair, and in a plane perpendicular to that direction.

Figure 5B:
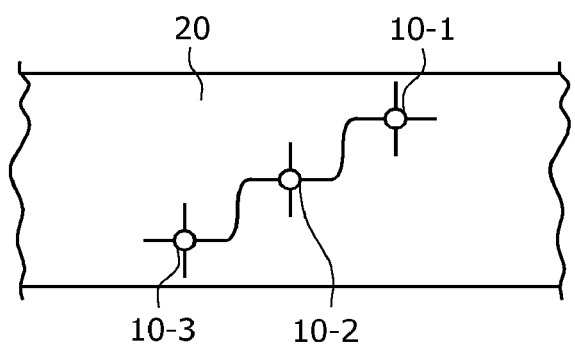

FIG. 5b shows the case in which the energy in each focus was just sufficient for the hair as a whole to break. It was found that in this case, the individual small areas of fracture around the foci smoothly interconnected along lines of fracture therebetween. In other words, clear visual signs of a kind of co-operation between the mechanical effects of LIOB in the individual foci show up. As a matter of fact, the total energy needed in this case was less, up to about 50% lower, than the total energy in a case wherein the pulses where supplied separated in time, even though the focal spots were in the same target positions. Of course, this energy will be lowest when the foci are on a line in the preferential plane of fracture, since then the interfocal distance is shortest.

Figure 5C:
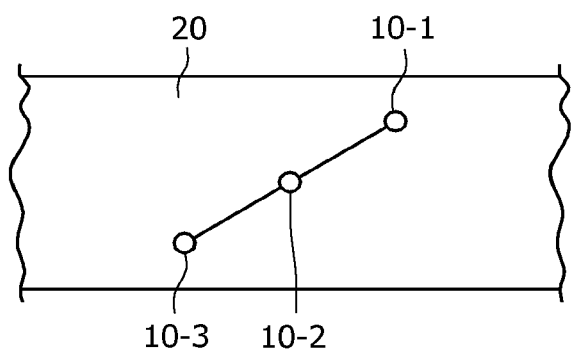

FIG. 5c shows a case similar to that in FIG. 5b, but the energy in the individual foci is somewhat higher, It was found that, even at only a slight increase of the energy above the level in FIG. 5b, the preferential directions of fracture were suppressed, and the hair broke simply in a plane through the foci. The result was a very smooth surface of fracture, as compared to a step-like surface in the case of FIG. 5b. This smoothness of the surface of fracture is another proof of the added value of co-operating mechanical effects due to substantially simultaneously generated LIOB pulses.

The invention claimed is:

1. A method for shortening hair, the method comprising acts of:
   generating a plurality of laser pulses overlapping in time and each having a pulse duration;
   focusing the plurality of laser pulses into a plurality of spatially separated focal spots, with each of at least three laser pulses focused in respective focal spots having a peak power density within the respective focal spots at least equal to a first Characteristic threshold value at which a laser induced optical breakdown phenomenon occurs in the hair wherein fractures in the hair result between the respective focal spots and below a second characteristic threshold value at which a laser induced optical breakdown phenomenon occurs in skin tissue, wherein the act of generating the plurality of laser pulses comprises an act of generating the plurality of laser pulses to reach the first characteristic threshold value after a start of each corresponding laser pulse in a time span of less than half of the pulse duration; and
   positioning the respective at least three focal spots into respective target positions within a single hair such that only one of the plurality of laser pulses occur in each of the at least three focal spots.

2. The method according to claim 1, wherein the act of generating the plurality of laser pulses comprises an act of generating the plurality of laser pulses to reach the first characteristic threshold value after the start of each corresponding laser pulse in the time span of less than 25% of the pulse duration.

3. The method according to claim 1, wherein the act of generating the plurality of laser pulses comprises an act of generating the plurality of laser pulses to reach the peak power density after the start of each corresponding laser pulse in the time span of less than half of the pulse duration.

4. The method according to claim 1, wherein the act of generating the plurality of laser pulses comprises an act of generating the plurality of laser pulses to reach the peak power density after the start of each corresponding laser pulse in the time span of less than 25% of the pulse duration.

5. The method according to claim 1, wherein the act of positioning comprises an act of positioning the respective at least three focal spots into respective target positions within a plane that extends substantially perpendicular to a direction of a shaft of the single hair.

6. The method according to claim 1, wherein the act of positioning comprises an act of positioning all of the plurality of spatially separated focal spots within the single hair.

7. The method according to claim 1, wherein the act of positioning comprises an act of positioning all of the plurality of spatially separated focal spots into respective target positions that form a pattern of a three dimensional tetrahedron within the single hair.

8. The method according to claim 7, wherein the three dimensional tetrahedron is an equilateral tetrahedron.

9. The method according to claim 1, wherein the act of positioning comprises an act of positioning all of the plurality of spatially separated focal spots to occur within a plane with 10 µm to 25 µm between contiguous respective focal spots.

10. The method according to claim 1, wherein the act of positioning comprises an act of positioning the respective at least three focal spots into respective target positions such that a focal spot is either positioned substantially within a medulla of the single hair with an increased power over each of others of the plurality of spatially separated focal spots not positioned substantially within the medulla or positioning a focal spot within the medulla is avoided.

11. The method according to claim 1, wherein the act of generating the plurality of laser pulses comprises an act of multiplying an incident beam of laser pulses into a plurality of substantially simultaneous outgoing beams of laser pulses.

12. The method according to claim 1, wherein the act of generating the plurality of laser pulses comprises an act of generating the plurality of laser pulses with a temporal profile of power density such that more than 70% of a total energy in each pulse is delivered after reaching the peak power density with a total energy applied by the plurality of laser pulses to the single hair of 1.5 mJ to 3 mJ.

13. The method according to claim 1, comprising an act of setting the peak power density within the respective focal spots to be between 60% and 95% of the second characteristic threshold value.

14. The method according to claim 1, comprising an act of setting the peak power density within the respective focal spots to be between 70% and 85% of the second characteristic threshold value.

15. The method according to claim 1, comprising an act of setting the peak power density to between $5.5 \cdot 10^{11}$ W/cm$^2$ and $7 \cdot 10^{11}$ W/cm$^2$ with a pulse duration of 8-10 ns.

* * * * *